United States Patent [19]

Douglas et al.

[11] 4,016,214

[45] Apr. 5, 1977

[54] PREPARATION OF ETHYNYLBENZENES

[75] Inventors: George Henry Douglas, Malvern; Norman J. Santora, Roslyn, both of Pa.

[73] Assignee: William H. Rorer, Inc., Fort Washington, Pa.

[22] Filed: Sept. 23, 1975

[21] Appl. No.: 615,957

Related U.S. Application Data

[62] Division of Ser. No. 523,109, Nov. 12, 1974, Pat. No. 3,952,067.

[52] U.S. Cl. .................. 260/649 F; 260/455 R; 260/465 K; 260/479 R; 260/576; 260/577; 260/578; 260/562 R; 260/562 F; 260/592; 260/607 A; 260/609 R; 260/612 D; 260/612 R; 260/618 D; 260/619 D; 260/620; 260/621 R; 260/645; 260/646; 260/649 R; 260/649 DP; 260/650 R; 260/650 F; 260/651 R; 260/668 R

[51] Int. Cl.$^2$ .................. C07C 15/09; C07C 15/14; C07C 25/24; C07C 79/10

[58] Field of Search ........ 260/678, 651 HA, 668 R, 260/645, 646, 649 F, 649 DP, 649 R, 650 R, 650 F

[56] References Cited

UNITED STATES PATENTS 3,418,385  12/1968  Skinner .................. 260/678 X
3,758,622  9/1973  Watson et al. ................. 260/668 R

*Primary Examiner*—Dolph H. Torrence
*Attorney, Agent, or Firm*—James A. Nicholson

[57] ABSTRACT

Process for preparing ethynylbenzene compounds by the dehalogenation of $\beta,\beta,\alpha$-trichlorophenylethane compounds is described.

9 Claims, No Drawings

PREPARATION OF ETHYNYLBENZENES

This is a division of application Ser. No. 523,109, filed Nov. 12, 1974, now U.S. Pat. No. 3,952,067.

This invention describes a novel process of preparing ethynylbenzene compounds and derivatives represented by the generic structure which is described by the general formula I;

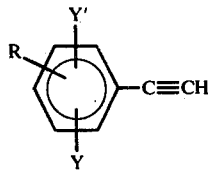

where:
R is
  alkyl,
  cycloalkyl,
  alkylcycloalkyl,
  aryl or
  substituted aryl where the substituent is Y''; and
Y, Y' and Y'' are
  hydrogen,
  alkyl,
  halo,
  nitro,
  amino,
  acylamino,
  mono and diloweralkylamino,
  mercapto,
  acylthio,
  loweralkylthio,
  loweralkylsulfinyl,
  loweralkylsulfonyl,
  hydroxy,
  loweralkoxy,
  acyloxy,
  haloloweralkyl,
  cyano or
  acetyl.

The para position is the preferred position for the R substituents.

The meta position is the preferred position for the Y and Y' substituents, and the ortho position is the preferred position for the Y'' substituents.

More specifically, this invention describes a process for preparing chemical compounds which have the preferred chemical structures described by formulae II–IV:

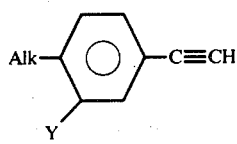

where Alk is alkyl having 3–7 carbon atoms.

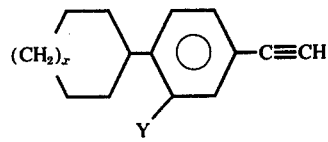

where $x$ is 0–2.

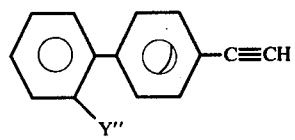

Those compounds which are even more preferred are described by formulae II–III:
where:
Y is
  hydrogen,
  halo,
  nitro,
  cyano,
  loweralkylsulfonyl or
  haloloweralkyl; and
$x = 1$.

The more preferred compounds of formula IV are those where Y'' is halo.

Compounds which are most preferred are those where Y is halo and chloro is particularly preferred.

In the descriptive portions of this invention the following definitions apply:

"Alkyl" refers to a loweralkyl hydrocarbon group containing from 1 to about 7 carbon atoms which may be straight chained or branched.

"Alkenyl" refers to an unsaturated or partially unsaturated hydrocarbon group containing from 2 to about 7 carbon atoms which may be straight chained or branched.

"Cycloalkyl" refers to a hydrocarbon ring having up to about seven carbon atoms.

"Aryl" refers to any benzenoid or non-benzenoid aromatic group but preferably phenyl.

"Alkoxy" refers to a loweralkoxy group containing from 1 to about 6 carbon atoms which may be straight chained or branched.

"Acyl" refers to any organic radical derived from an organic acid by the removal of its hydroxyl group such as formyl, acetyl, propionyl.

The compounds of this invention may be prepared by the following process.

A Friedel-Crafts reaction of a substitutedbenzene and acetyl chloride results in the preparation of a p-substitutedacetophenone. The resultant acetophenone may then be (a) halogenated, (b) nitrated or (c) alkylated to obtain the corresponding 3-halo, 3-nitro, or 3-alkyl-4-substituted-acetophenones. Chlorination or bromination may be carried out in the presence of a small amount of iodine dissolved in an inert solvent such as carbon tetrachloride. A solution of chlorine or bromine is then added while the temperature is held near 0° C. Nitration is carried out with fuming nitric acid at about 0° C. Alkylation is carried out under Friedel-Crafts conditions with an alkyl halide and aluminum chloride. The following reaction equations illustrate these methods.

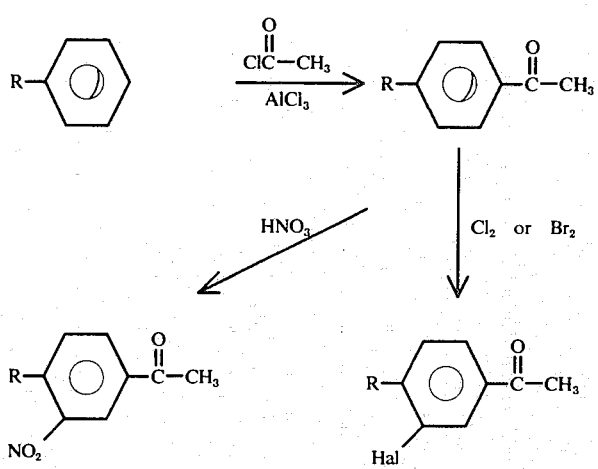

where R is as described above and Hal is chloro or bromo.

Appropriately desired end products having various Y and Y' substituents can be prepared by using suitable reactions in order to convert one group to another. Thus, for example, a 3-halo-4-substituted-acetophenone in which halo is chloro or bromo may be a. reacted with cuprous cyanide in quinoline at about 150° C to produce a 3-cyano-4-substitutedacetophenone.

b. reacted with trifluoromethyliodide and copper powder at about 150° C in dimethylformamide to obtain a 3-trifluoromethyl-4-substituted-acetophenone [as described in Tetrahedron Letters: 47, 4095 (1959)];

c. reacted with cuprous methanesulfinate in quinoline at about 150° C to obtain a 3-methylsulfonyl-4-substitutedacetophenone.

A 3-nitro-4-substitutedacetophenone may be selectively hydrogenated to the corresponding amine. A 3-amine-4-substitutedacetophenone may then be a. mono- or dialkylated with loweralkyl halides or sulfates or acylated with loweracyl chlorides or anhydrides;

b. diazotized to the diazonium fluoroborate which is then thermally decomposed to the 3-fluoro-4-substitutedacetophenone;

c. diazotized and heated in an aqueous medium to form the 3-hydroxy-4-substitutedacetophenone or heated in an alcohol to form the 3-alkoxy-4-substitutedacetophenone. The hydroxyl group may also be alkylated with loweralkyl halides or sulfates to the alkoxyl group or acylated with loweracyl chlorides or anhydrides to the acyloxy compound in the presence of a tertiary amine such as pyridine;

d. diazotized followed by a Sandmeyer type reaction to yield the halo group;

e. diazotized and heated with an aqueous solution of potassium iodide to prepare the 3-iodo-4-substitutedacetophenone;

f. diazotized and followed by addition of cuprous cyanide to obtain the 3-cyano-4-substitutedacetophenone which in turn may be esterified with an alcohol or hydrolyzed to the amide or carboxylic acid of the acetophenone;

g. diazotized followed by reaction with potassium ethylxanthate followed by hydrolysis to obtain 3-mercapto-4substitutedacetophenone which can be esterified to a 3-mercapto-4-substitutedacetophenone. This in turn can be lower alkylated to the lower alkylthio and oxidized to the loweralkylsulfinyl and loweralkylsulfonyl groups or acylated to the acylthio compounds.

A second nitration or halogenation may be carried out on the 3-substitutedacetophenone. This may be carried out at any appropriate stage of the synthesis in order to obtain the desired substituents. Thus, for example, a 3-chloro-4-substitutedacetophenone may be nitrated as above to obtain a 3-chloro-5-nitro-4-substitutedacetophenone. Halogenation of a 3-chloroacetophenone gives a 2,5-disubstituted compound. A 3-nitro-4-substitutedacetophenone can be nitrated to give a 3,5-dinitro-4-substitutedacetophenone.

Controlled halogenation of the substitutedacetophenone is carried out using elemental halogen such as chlorine in the presence of a small amount of iodine and dissolved in an inert solvent such as carbon tetrachloride while the temperature is held near 0° C. When the substitutent desired in the 3-position of the phenyl ring is also a chloro group then the starting material is the substituted acetophenone. This results in the additional chlorination at the 3-position.

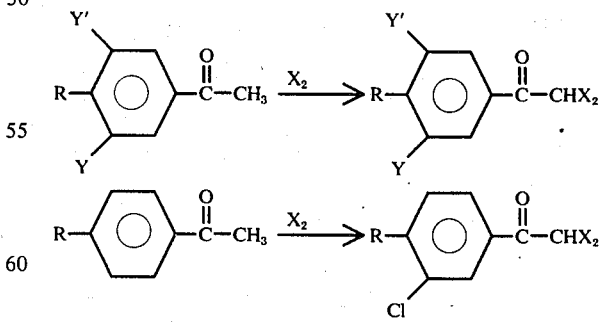

Sodium borohydride reduction of the halogenated acetophenone yields the corresponding benzyl alcohol. This reduction may also be carried out by catalytic hydrogenation provided the groups present are not sensitive to this reaction.

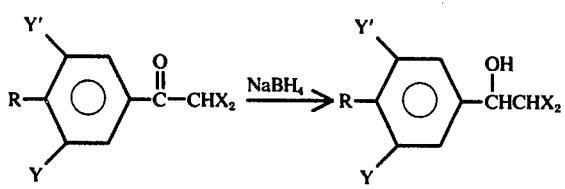

The latter benzyl alcohol may next be treated with a halogenating agent such as phosphorus trihalide, phosphorus pentahalide, phosphorus oxyhalide, sulfurylhalide, thionylhalide or sulfur halide to obtain the corresponding β,β,α-trichlorophenylethane product.

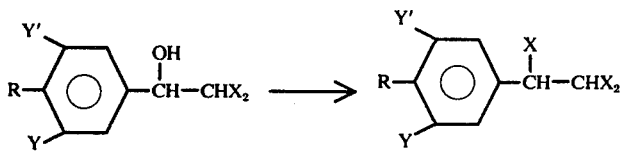

Elimination of chlorine using methyl lithium or the like such as alkyl lithium, or alkyl sodium, or sodamide, or lithium diisopropylamide results in the desired ethynylbenzene compounds. This is preferably carried out in an inert atmosphere and lower temperatures may involve stepwise elimination.

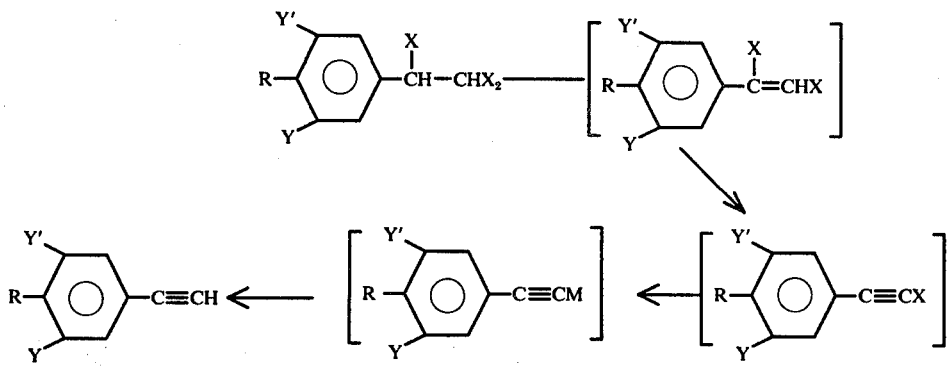

The final products of this invention and their preparation are disclosed and claimed in Belgian Pat. No. 809,147.

These compounds are most useful since they provide significant effectiveness as anti-inflammatory agents as well as manifesting desirable analgesic and anti-pyretic properties.

The instant process provides the advantages that the compounds are prepared from more readily accessible agents which are economically useful. The reaction steps involved are relatively routine compared to the more complex synthesis previously described. This results in the advantage of elimination of costly equipment and labor.

The various Y, Y' and Y'' substituents may also be prepared at various steps of the synthesis as previously described. Thus, halogenation or nitration may be carried out on the substituted benzylalcohol or β,β,α-trichlorophenylethane products.

EXAMPLE 1

3-Chloro-4-cyclohexyl-1-ethynylbenzene

A. p-Cyclohexylacetophenone

To a suspension of anhydrous aluminum chloride (467 g.; 3.5 moles) in carbon tetrachloride (2 l.) is added acetyl chloride (275 g.; 249 cc., 3.5 moles) during 15 minutes with vigorous stirring and cooling in an ice-bath. Cyclohexylbenzene (481 g.; 3.0 moles) is added dropwise over a period of 3 hours, keeping the temperature below 5°. After addition is complete, the product is stirred for another hour before hydrolyzing by pouring into ice and hydrochloric acid with stirring. The organic phase is washed with successive portions of dilute hydrochloric acid, sodium carbonate, and water, and distilled to give p-cyclohexylacetophenone, (b.p. 88°–95.5°/ 0.05 mm.).

When cyclohexylbenzene in the above example is replaced with cyclopentylbenzene, cycloheptylbenzene, 2'-methylcyclohexylbenzene, i-propylbenzene, i-butylbenzene, and t-butylbenzene, then the products prepared are p-cyclopentylacetophenone, p-cycloheptylacetophenone, p-(2'methylcyclohexyl)acetophenone, p-i-propylacetophenone, p-i-butylacetophenone and p-t-butylacetophenone.

B. α,α,3-Trichloro-4-cyclohexylacetophenone

To p-cyclohexylacetophenone (50.5 g.; 0.25 moles) dissolved in carbon tetrachloride (300 cc) at ice-bath temperature is added $Cl_2$ (0.25 moles) dissolved in carbon tetrachloride. Then, iodine (3.9 g.) is added followed by excess chlorine dissolved in carbon tetrachloride. The reaction mixture is allowed to come to room temperature overnight. The solvent is removed and the residue is taken up in ether and washed with 10% $NaHSO_3$, saline, and dried with ($Na_2SO_4$). The solvent is removed and the residue distilled to give α,α,3-trichloro-4-cyclohexylacetophenone.

When p-cyclohexylacetophenone is replaced in the above example by the acetophenones of part A, then the products prepared are shown in Table I, below.

TABLE I

α,α,3-trichloro-4-cyclopentylacetophenone
α,α,3-trichloro-4-cycloheptylacetophenone
α,α,3trichloro-4-(2'-methylcyclohexyl)acetophenone
α,α,3-trichloro-4-i-propylacetophenone
α,α,3-trichloro-4-i-butylacetophenone
α,α,3-trichloro-4-t-butylacetophenone C. β,β-dichloro-α-(3-chloro-4-cyclohexylphenyl)ethanol To α,α,3-trichloro-4-cyclohexylphenylacetophenone (68.6 g.; 0.22 moles) in isopropanol (500cc) is added sodium borohydride (2.6 g.; 20% excess) in successive portions. The reaction mixture is heated to 60° and allowed to come to room temperature over several hours with stirring. The reaction mixture is diluted with water and acidified with 10% hydrochloric acid (40 cc) and then extracted into ether. The ethereal fraction is washed with water, 10% NaHCO₃, and saline until the washings are neutral. The organic phase is dried over Na₂SO₄ and the solvent removed to give β,β-dichloro-α-(3-chloro-4-cyclohexylphenyl)ethanol.

When α,α,3-trichloro-4-cyclohexylphenylacetophenone is replaced in the above example by the acetophenones of Table I then the corresponding benzylalcohol of Table II, below, is prepared.

TABLE II

β,β-dichloro-α-(3-chloro-4-cyclopentylphenyl)ethanol.
β,β-dichloro-α-(3-chloro-4-cycloheptylphenyl)ethanol.
β,β-dichloro-α-[3-chloro-4-(2'methylcyclohexyl)-phenyl]ethanol.
β,β-dichloro-α-(3-chloro-4-i-propylphenyl)ethanol.
β,β-dichloro-α-(3-chloro-4-i-butylphenyl)ethanol.
β,β-dichloro-α-(3-chloro-4-t-butylphenyl)ethanol.

D. β,β,α,3-Tetrachloro-4-cyclohexylphenylethane

β,β-Dichloro-α-(3-chloro-4-cyclohexylphenyl)ethanol (67.5 g.; 0.22 moles) is heated with thionyl chloride (110 ml) containing 1 drop of pyridine until solution is obtained. The heating is discontinued and the reaction is allowed to proceed at room temperature for 12 hours. The reaction mixture is heated for an additional hour and the thionyl chloride removed, chased by benzene several times and distilled to give β,β,α,3-tetrachloro-4-cyclohexylphenylethane.

When β,β-dichloro-α-(3-chloro-4-cyclohexylphenyl)ethanol in the above example is replaced by the phenyl ethanols of Table II, then the corresponding tetrachloro compound of Table III below is prepared.

TABLE III

β,β,α,3-tetrachloro-4-cyclopentylphenylethane
β,β,α,3-tetrachloro-4-cycloheptylphenylethane
β,β,α,3-tetrachloro-4-(2'-methylcyclohexyl)phenylethane
β,β,α,3-tetrachloro-4-i-propylphenylethane
β,β,α,3-tetrachloro-4-i-butylphenylethane
β,β,α,3-tetrachloro-4-t-butylphenylethane E. 3-Chloro-4-cyclohexyl-1-ethynylbenzene β,β,α,3-tetrachloro-4-cyclohexylphenylethane (55.8 g.; 0.17 moles) is dissolved in anhydrous ether (100 ml). The solution is cooled in an ice-bath with stirring under nitrogen. Methyl lithium (2.3 M in ether; 300 cc) is added dropwise and the mixture stirred in the icebath for 2.5 hours before destroying the excess methyl lithium with ice. The ethereal fraction is washed thoroughly with saline until the washings are neutral. Removal of solvent gives 3-chloro-4-cyclohexyl-1-ethynylbenzene (b.p. 82°–88°/0.15 m).

When β,β,α,3-tetrachloro-4-cyclohexylphenylethane in the above example is replaced by the tetrachloro compounds of Table III, then the corresponding ethynylbenzene of Table IV below is prepared.

TABLE IV 3-chloro-4-cyclopentyl-1-ethynylbenzene
3-chloro-4-cycloheptyl-1-ethynylbenzene
3-chloro-4-(2'-methylcyclohexyl)-1-ethynylbenzene
3-chloro-4-i-propyl-1-ethynylbenzene
3-chloro-4-i-butyl-1-ethynylbenzene
3-chloro-4-t-butyl-1-ethynylbenzene When methyl lithium in the above reactions is replaced by an equimolar amount of an alkyl lithium reagent, lithium diisopropylamide in tetrahydrofuran or NaNH₂ in liquid ammonia then the same products are prepared.

EXAMPLE 2

3-Nitro-4-cylcohexyl-1-ethynylbenzene

A. 3-Nitro-4-cyclohexylacetophenone

Ethyl p-cyclohexylacetophenone (0.666 mole) is added to ice-cold concentrated sulfuric acid (18 ml) and stirred with cooling for 5 minutes. Concentrated nitric acid (Sp. G. 1.51) (2.5 ml) is added dropwise, maintaining the temperature between 30° and 40° by water cooling when necessary. After addition of the nitric acid is complete, the mixture is stirred for ½ hour, then poured into water. The mixture is made alkaline with sodium hydroxide, then extracted with ether. The ether extract is washed, dried over sodium sulfate, evaporated and the residue is fractionally distilled to obtain 3-nitro-4-cyclohexylacetophenone.

When the acetophenones of Example 1 are used in place of p-cyclohexylphenylacetophenone in the above example, then the corresponding nitrated product is prepared.

When 3-nitro-4-cyclohexylacetophenone is used in place of p-cyclohexylacetophenone in part A of Example 1, and the corresponding reactions are carried out according to parts B–E of Example 1, then the product obtained in 3-nitro-4-cyclohexyl-1-ethynylbenzene.

When the acetophenones of Example 1 are used in the above example and then the corresponding reactions are carried out according to parts A–E of Example 1, the products obtained are listed in Table IV below:

TABLE IV 3-nitro-4-cyclopentyl-1-ethynylbenzene
3-nitro-4-cycloheptyl-1-ethynylbenzene
3-nitro-4-(2'-methylhexyl)-1-ethynylbenzene
3-nitro-4-i-propyl-1-ethynylbenzene
3-nitro-4-i-butyl-1-ethynylbenzene
3-nitro-4-t-butyl-1-ethynylbenzene
3-nitro-1-ethynylbiphenyl

EXAMPLE 3

When cyclohexylbenzene is replaced in Example 1 by an equimolar amount of biphenyl and reaction steps A–E are followed accordingly, then the product prepared is p-biphenylacetylene (m.p. 81°–83.5° C).

EXAMPLE 4

When cyclohexylbenzene is replaced in Example 1 by an equimolar amount of 2-chlorobiphenyl and reaction steps A–E are followed accordingly, then the product prepared is 2'-chloro-4-ethynylbiphenyl.

(Calc'd: C, 79.06; H, 4.27; Cl, 16.67. Found: C, 78.86; H, 4.28; Cl, 16.61).

Example 5

Compounds having the desired R, Y, Y' and Y'' substituents may be carried out accordingly.

We claim:

1. A process for preparing a substituted ethynylbenzene compound of the formula:

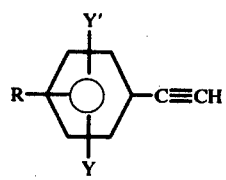

where:
R is
  alkyl,
  cycloalkyl,
  alkylcycloalkyl,
  aryl or
  substituted aryl where the substituent is Y''; and
Y, Y' and Y'' are
  hydrogen,
  halo or
  nitro
which comprises in sequence the steps of:
a. chlorinating a substituted acetophenone compound of the formula:

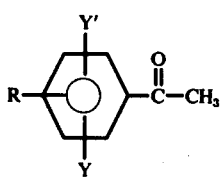

where R, Y and Y' are as described above, with elemental chlorine in the presence of iodine in an inert solvent to obtain a compound of the formula:

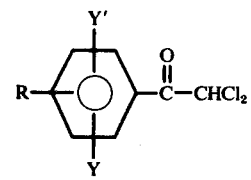

where R, Y, and Y' are as described above;
b. reducing said chlorinated product of step (a) with sodium borohydride to the corresponding benzyl alcohol of the formula:

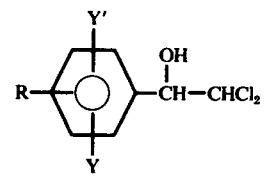

where R, Y, and Y' are as described above;
c. halogenating said benzyl alcohol of step (b) with an agent selected from phosphorus trihalide, phosphorus pentahalide, phosphorus oxyhalide, sulfuryl halide, thionyl halide or sulfur halide to obtain a $\beta,\beta,\alpha$-trichlorophenylethane compound of the formula:

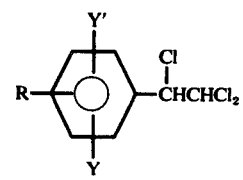

where R, Y and Y' are as described above, and
d. reacting said $\beta,\beta,\alpha$-trichlorophenylethane compounds of step (c) with an organolithium, organosodium, sodamide or lithium organoamide compound to obtain the desired substituted ethynylbenzene compound.

2. A process of claim 1 where R is in the para-position.
3. A process of claim 2 where Y' is hydrogen and Y is in the meta-position.
4. A process of claim 3 where R is alkyl having 3–7 carbon atoms.
5. A process of claim 3 where R is cycloalkyl having 5–7 carbon atoms.
6. A process of claim 3 where Y is hydrogen, R is phenyl or substituted phenyl, and where Y'' is in the ortho position.
7. A process of claim 6 where Y'' is halo.
8. A process of claim 7 where Y'' is fluoro.
9. A process of claim 7 where Y'' is chloro.

* * * * *